United States Patent [19]

Kurono et al.

[11] Patent Number: 4,528,143
[45] Date of Patent: Jul. 9, 1985

[54] PROCESS FOR THE PREPARATION OF 4-CHLORO-2-NITROBENZONITRILE

[75] Inventors: Masayasu Kurono, Nagoya; Takuji Yamaguchi, Kuwana; Toshinao Usui, Gifu, all of Japan

[73] Assignee: Sanwa Kagaku Kankyusho Co. Ltd., Nagoya, Japan

[21] Appl. No.: 546,866

[22] Filed: Oct. 31, 1983

[30] Foreign Application Priority Data

Nov. 26, 1982 [JP] Japan ................................ 57-206020

[51] Int. Cl.³ ............................................. C07C 121/52
[52] U.S. Cl. ................................................. 260/465 G
[58] Field of Search ..................................... 260/465 G

[56] References Cited

U.S. PATENT DOCUMENTS 1,672,253 6/1928 Giles .............................. 260/465 R
3,351,651 11/1967 Rothman ........................ 260/465 G
3,644,471 2/1972 Di Bella ......................... 260/465 G

*Primary Examiner*—Dolph H. Torrence
*Attorney, Agent, or Firm*—Charles A. Muserlian

[57] ABSTRACT

A process for the preparation of 4-chloro-2-nitrobenzonitrile, which comprises a step for subjecting 2,5-dichloronitrobenzene to a reaction with copper (I) cyanide.

6 Claims, No Drawings

PROCESS FOR THE PREPARATION OF 4-CHLORO-2-NITROBENZONITRILE

FIELD OF THE INVENTION

The present invention relates to a novel process for the preparation of 4-chloro-2-nitrobenzonitrile.

The compound is one of useful intermediates for preparing various pharmaceutical agents and other chemicals, for instance is important as an intermediate for synthesizing 5-(4-chloro-5-sulphamoyl-2-thenylamino phenyl)-1H-tetrazole which is useful as one of diuretic agents.

PRIOR ART

Hitherto, it has been known that the compound can be prepared by heating 4-chloro-2-nitro benzoic acid with methane sulfonamide and phosphorus pentachloride (DE-OS No. 21 26 720). This conventional method shows a good yield but has a problem in its industrial operation, since the raw material of 4-chloro-2-nitro benzoic acid is expensive to make higher the manufacturing cost.

OBJECTS OF THE INVENTION

An object of the invention is, therefore, to provide a novel process for the preparation of 4-chloro-2-nitrobenzonitrile, which is suitable for its industrial scale production, since the compound can be synthesized with use of a starting material available from a market in a reasonable price.

Another object of the invention is to provide a novel process for the preparation of 4-chloro-2-nitrobenzonitrile, which gives a relatively high yield.

SUMMARY OF THE INVENTION

According to the invention, the objects can be attained by a process for the preparation of 4-chloro-2-nitrobenzonitrile, which comprises a step for subjecting 2,5-dichloronitrobenzene to a reaction with copper (I) cyanide.

The starting material (2,5-dichloronitrobenzene) has been known as one of raw materials for dyes and is available from a market in a large amount and with a reasonable price.

For obtaining a nitrile compound from a corresponding aromatic halide, a method of using copper (I) cyanide in the presence or absence of a solvent has generally been adopted and in this case, some reports had been made to show a success of such reaction by adding a small amount of an inorganic cyanide. It is a technical common sense, however, that if there is an electron attractive group such as nitro group in ortho position of the starting compound, an undesirable side reaction proceeds and thus a higher yield of the objective compound can not be expected.

Having studied reaction conditions from various view points, the inventors found out a fact that a good result can be obtained by causing a reaction of 1.0 to 1.5 molar amount of copper (I) cyanide to 1.0 molar amount of 2,5-dichloronitrobenzene. The reaction can be carried out in the absence of a solvent but it is preferable to carry out in the presence of an inert solvent such as N,N-dimethylformamide, pyridine, N-methyl-pyrrolidone or the like for 2.0 to 6.0 hours at a temperature ranging from 140° to 170° C. The reaction may also be carried out by additionally adding a small amount of one or more inorganic cyanides such as potassium cyanide and sodium cyanide.

Among various experiments, a best result was obtained when 2,5-dichloronitrobenzene is subjected to a reaction with copper (I) cyanide in same molar amount, in the presence of 0.01 time molar amount of potassium cyanide and in 0.9 times molar amount of N,N-dimethylformamide for 4 to 6 hours at a temperature ranging from 160° to 170° C.

The desired or objective 4-chloro-2-nitrobenzonitrile can be obtained in a higher yield by pouring the resulting reaction mixture into a cooled solvent such as toluene or benzene, stirring the solution at a room temperature, filtering off unsoluble inorganic compounds, distilling off the solvent in the filtrate and then washing the residue with carbon tetrachloride.

4-Chloro-2-nitrobenzonitrile to be obtained through said simple post-treatment contains almost no impurity.

PREFERRED EMBODIMENT OF THE INVENTION

The invention will now be further explained with reference to Examples.

EXAMPLE 1

4-Chloro-2-nitrobenzonitrile

A mixture of 230.4 g (1.20 mol) of 2,5-dichloronitrobenzene, 108 g (1.20 mol) of copper (I) cyanide, and 0.80 g (0.012 mol) of potassium cyanide in 80 ml (1.04 mol) of N,N-dimethylformamide was heated for 5.5 hours at 165°–170° C.

The reaction mixture was poured slowly into 1.2 l of cold toluene and followed by stirring for 13 hours at room temperature. The precipitate was filtered and washed with 100 ml of ethyl acetate. After concentration of the combined filtrate, the residue was washed with 140 ml of carbon tetrachloride to give 125 g of 4-chloro-2-nitrobenzonitrile as pale yellow crystals. From the solution of carbon tetrachloride, more 35 g of 4-chloro-2-nitrobenzonitrile were obtained. Total yield was 160 g (73.1%).

| | |
|---|---|
| m.p. 90~93° C. | |
| IR spectrum: $\nu_{max}^{KBr}$ cm$^{-1}$ | 2240 (—CN), 1525 (—NO$_2$) 1350 (—NO$_2$) |
| NMR spectrum δppm (CDCl$_3$) | 8.00 (2H, s, aromatic 5-H, 6-H) 8.47 (1H, s, aromatic 3-H) |
| MS spectrum m/e | 182 (M$^+$) |

EXAMPLE 2

A mixture of 7.7 g (0.040 mol) of 2,5-dichloronitrobenzene and 4.0 g (0.044 mol) of copper (I) cyanide in 4.0 ml (0.05 mol) of N,N-dimethylformamide was refluxed for 3.5 hours. The reaction mixture was poured slowly into 39 ml (0.40 mol) of ethyl acetate and followed by stirring for 10 hours at room temperature. The precipitate was filtered and washed with 3 ml of ethyl acetate. After concentration of the combined filtrate, the residue gave 4.6 g (63.0%) of 4-chloro-2-nitrobenzonitrile purified by the procedure of Example 1.

EXAMPLE 3-9

4-Chloro-2-nitrobenzonitrile was prepared with the method as shown in Table-1. Purification was followed by the procedure of Example 1.

TABLE-1

| Example | 2,5-Dichloro-nitrobenzene (mole) | Copper (I) cyanide (mole) | Inorganic cyanide (mole) | N,N—Dimethyl-formamide (mole) | Reaction time (hr) | Reaction temperature (°C.) | Yield of 4-Chloro-2-nitro-benzonitrile (%) |
|---|---|---|---|---|---|---|---|
| 3 | 1 | 1.1 | — | 3.25 | 3 | reflux | 60.1 |
| 4 | 1 | 0.9 | — | 2.6 | 4 | " | 50.3 |
| 5 | 1 | 1.0 | 1.0 (NaCN) | 5.0 | 12 | " | 56.0 |
| 6 | 1 | 1.0 | 0.1 (NaCN) | 5.0 | 12 | " | 47.0 |
| 7 | 1 | 1.0 | 0.1 (KCN) | 5.0 | 6 | " | 70.0 |
| 8 | 1 | 1.0 | 0.01 (KCN) | 3.0 | 5 | " | 70.2 |
| 9 | 1 | 1.1 | 0.055 (KCN) | 3.0 | 5 | " | 43.0 |

We claim:

1. A process for the preparation of 4-chloro-2-nitrobenzonitrile comprising reacting 2,5-dichloronitrobenzene with copper (I) cyanide in an inert solvent in the presence of an inorganic cyanide at a temperature of 140° to 170° C. for 2.6 to 6.0 hours.

2. A process as claimed in claim 1 wherein said copper (I) cyanide is added in 0.9 to 1.5 molar amount based on 2,5-dichloronitrobenzene.

3. A process as claimed in claim 1 wherein said solvent is selected from the group consisting of N,N-dimethylformamide, N-methylpyrolidone and pyridine.

4. A process as claimed in claim 1 wherein said inorganic cyanide is selected from the group consisting of potassium cyanide and sodium cyanide.

5. A process as claimed in claim 1 wherein said inorganic cyanide is added in 0.01 to 0.1 molar amount based on 2,5-dichloronitrobenzene.

6. A process as claimed in claim 1 further comprising pouring the resulting reaction mixture into toluene, filtering-off insoluble materials, distilling the filtrate to dryness and washing the residue with carbon tetrachloride.

* * * * *